(12) United States Patent
Siemionow

(10) Patent No.: US 9,724,369 B2
(45) Date of Patent: Aug. 8, 2017

(54) METHODS OF MAINTAINING FAT VOLUME

(71) Applicant: The Cleveland Clinic Foundation, Cleveland, OH (US)

(72) Inventor: Maria Siemionow, Chicago, IL (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/657,825

(22) Filed: Mar. 13, 2015

(65) Prior Publication Data

US 2015/0320802 A1    Nov. 12, 2015

Related U.S. Application Data

(60) Provisional application No. 61/953,123, filed on Mar. 14, 2014.

(51) Int. Cl.
| | | |
|---|---|---|
| *A61K 45/06* | (2006.01) | |
| *A61K 9/00* | (2006.01) | |
| *A61K 35/35* | (2015.01) | |
| *A61L 27/36* | (2006.01) | |

(52) U.S. Cl.
CPC ............ *A61K 35/35* (2013.01); *A61K 9/0019* (2013.01); *A61K 45/06* (2013.01); *A61L 27/3604* (2013.01); *A61L 2430/34* (2013.01)

(58) Field of Classification Search
None
See application file for complete search history.

(56) References Cited

FOREIGN PATENT DOCUMENTS

WO    WO 2009/124170 A1    10/2009

OTHER PUBLICATIONS

Auchincloss (1991) "Xenogenic Transplantation: Immunologic Issues and Future Prospects", New Therapeutic Strategies in Nephrology, Andreucci (ed.), by Kluwer Academic Press, New York, NY., 483-88.*
Shi, et al. (2006) "Granulocyte-macrophage colony-stimulating factor (GM-CSF) and T-cell responses: what we do and don't know", Cell Research, 16(2): 126-33.*
Uygur, et al. (2014) "Application of Epineural Sheath for Fat Graft Volume Maintenance", Plastic and Reconstructive Surgery, 137(Supp 4): 28.*
Siemionow, et al. (2011) "Peripheral Nerve Defect Repair With Epineural Tubes Supported With Bone Marrow Stromal Cells", Annals of Plastic Surgery, 67: 73-84.*
PCT/US2015/020550 Notification of Transmittal of the International Search Report and the Written Opinion of the International Searching Authority, or the Declaration dated Jun. 30, 2015 entitled "Methods of Maintaining Fat Volume."
PCT/US2015/020550 International Search Report dated Jun. 30, 2015 entitled "Methods of Maintaining Fat Volume."
PCT/US2015/020550 Written Opinion dated Jun. 30, 2015 entitled "Methods of Maintaining Fat Volume."
International Preliminary Report on Patentability, "Methods of Maintaining Fat Volume," PCT/US2015/020550, date of issuance Sep. 14, 2016.

* cited by examiner

*Primary Examiner* — Robert M Kelly
(74) *Attorney, Agent, or Firm* — Hamilton, Brook, Smith & Reynolds, P.C.

(57) ABSTRACT

In one aspect, the invention is directed to a method of delivering fat to one or more sites in an individual in need thereof comprising introducing an effective amount of one or more epineural sheaths comprising adipose tissue to the one or more sites in the individual. In another aspect, the invention is directed to a method of maintaining or augmenting (increasing) fat volume at one or more sites in an individual in need thereof comprising introducing an effective amount one or more epineural sheaths comprising adipose tissue to the one or more sites in the individual. The one or more epineural sheaths comprising adipose tissue is maintained under conditions in which the fat volume is maintained and/or augmented at the one or more sites in the individual.

17 Claims, 11 Drawing Sheets

Figure 3
Experimental Design
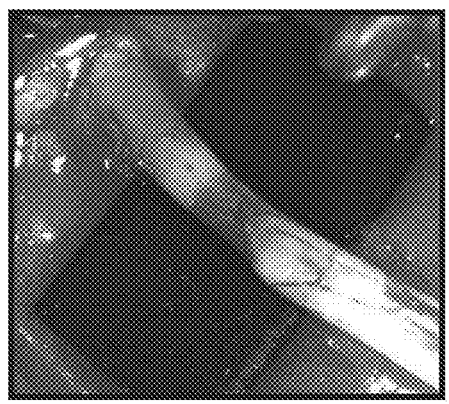
Group 1 (Control)
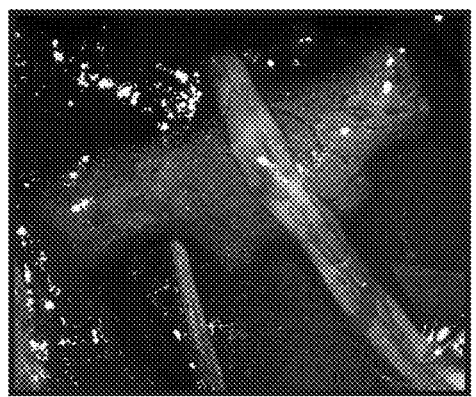
Group 2 (Fat graft)
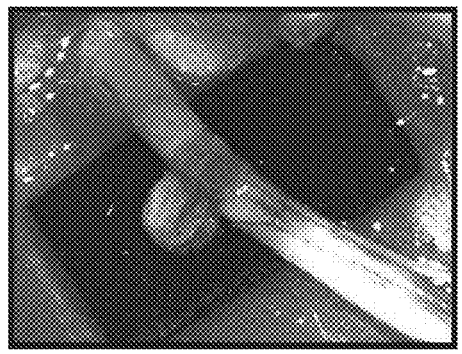
Group 3 (Isogenic ES)
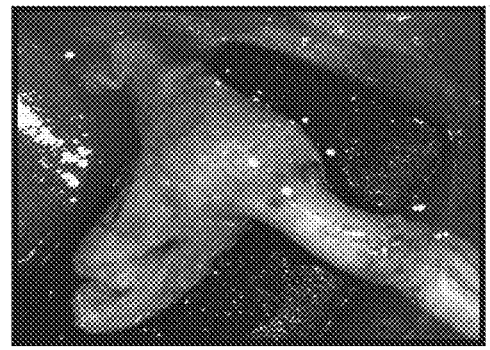
Group 4 (Allogenic ES)

Figure 4
Results
Macroscopic analysis
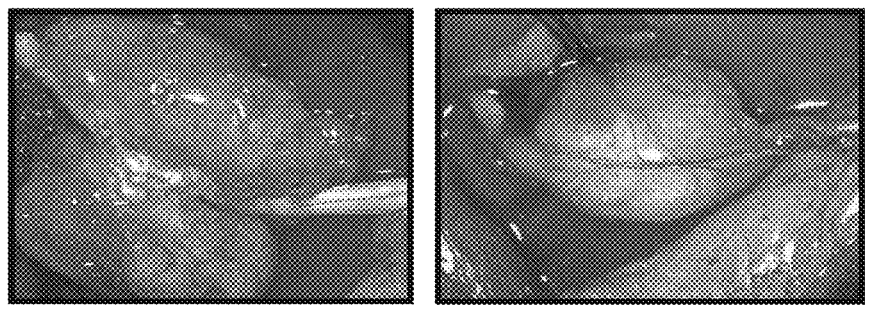
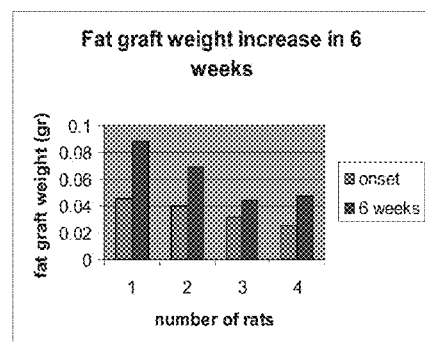
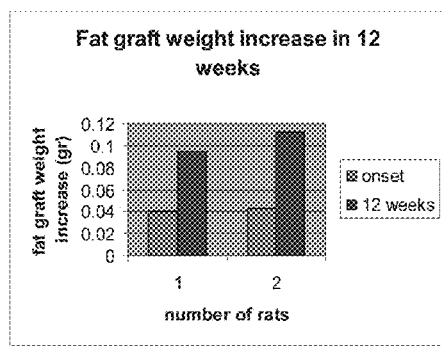
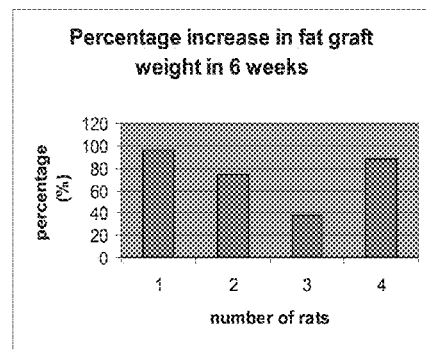
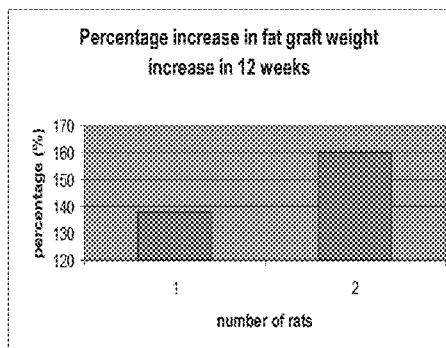

Results Immunohistostainig

- High expression of VEGF in isogenic ES (A)
- Significantly lower VEGF expression at control groups (B)
- Lowest VEGF expression at fat graft groups (C)

VEGF fluorescent expression (FITC green dye) in normal wound conditions with isogenic ES (A), control (B), and fat graft (C) applications. Blue color represents nuclei (Blue, DAPI) Magnification x200.

The sciatic nerve segment

The empty epineural tube

The empty epineural tube

Fat tissue chopping

Chopped fat tissue inside the syringe

Fat tissue implantation inside the epineural tube

The epineural jacket

The epineural jacket

The epineural jacket

The epineural jacket implanted into dorsal subcutaneous region

The epineural jacket implanted into dorsal subcutaneous region

FIGS. 14A-14F

Animal #851

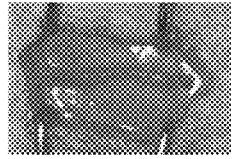 

A. Group 1 Epineural Jacket+ Fat day of implantation  B. and C. Group 1 Epineural Jacket + Fat 1 week after implantation.

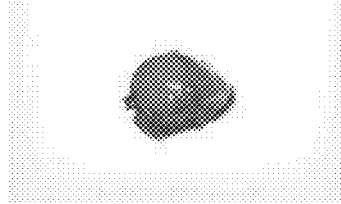

D. Group 1.Cross sectional view of the Epineural Jacket filled with Fat ( presented on Fig. B above) one week after implantation showing fat volume maintenance inside the epineural jacket –see Table 1 .

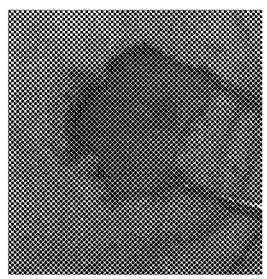 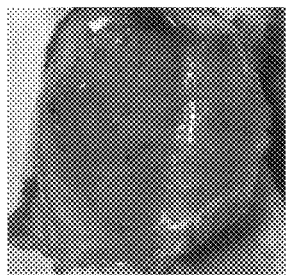

E. Group 2. Fat tissue alone at day of implantation  F. Group 2. Fat tissue alone 1 week after implantation showing dispersion of the fat tissue into small pieces which confirms that fat volume was not maintained without coverage wit epineural jacket – see Table 1.

METHODS OF MAINTAINING FAT VOLUME

RELATED APPLICATION

This application claims the benefit of U.S. Provisional Application No. 61/953,123, filed on Mar. 14, 2014. The entire teachings of the above application is incorporated herein by reference.

BACKGROUND OF THE INVENTION

A variety of surgical interventions (e.g., reconstructive or plastic surgery) involve the introduction of fat to an individual. However, a major issue with current methods of fat delivery is that the injected fat cannot be maintained for long periods of time, and thus, multiple injections are required to maintain or supplement the fat volume in the individual. This increases the cost, side effects and complications (e.g., infection, fat necrosis, granuloma formation, wound healing issues) of such procedures due to multiple surgical interventions.

A need exists for improved methods of introducing fat into an individual in need thereof.

SUMMARY OF THE INVENTION

In one aspect, the invention is directed to a method of delivering fat to one or more sites in an individual in need thereof comprising introducing an effective amount of one or more epineural sheaths comprising adipose tissue to the one or more sites in the individual.

In another aspect, the invention is directed to a method of maintaining or augmenting (increasing) fat volume at one or more sites in an individual in need thereof comprising introducing an effective amount of one or more epineural sheaths comprising adipose tissue to the one or more sites in the individual. The one or more epineural sheaths comprising adipose tissue is maintained under conditions in which the fat volume is maintained and/or augmented at the one or more sites in the individual.

BRIEF DESCRIPTION OF THE DRAWINGS

FIG. 3 shows Groups 1, 2, 3 and 4 of a proof of principal experiment.

FIG. 4 shows macroscopic analysis that fat tissue increase in volume over time (6 weeks and 12 weeks) and was firmly attached to the nerve.

FIG. 14A-14E show: Group 1: Epineural jacket+fat at 0 week (FIG. 14A) and 1 week after implantation (FIG. 14B) Group 1: Epineural jacket+fat 1 week after implantation (FIG. 14C); Group 1: Cross sectional view (FIG. 14D) of the epineural jacket filled with fat (see FIG. 14C) one week after implantation showing fat volume maintenance inside the epineural jacket—see Table; Group 2: Fat tissue alone at day of implantation (FIG. 14E); Group 2: Fat tissue alone 1 week after implantation showing dispersion of the fat tissue into small pieces which confirms that fat volume was not maintained without coverage with epineural jacket (FIG. 14F)—see Table.

DETAILED DESCRIPTION OF THE INVENTION

Figure 1:
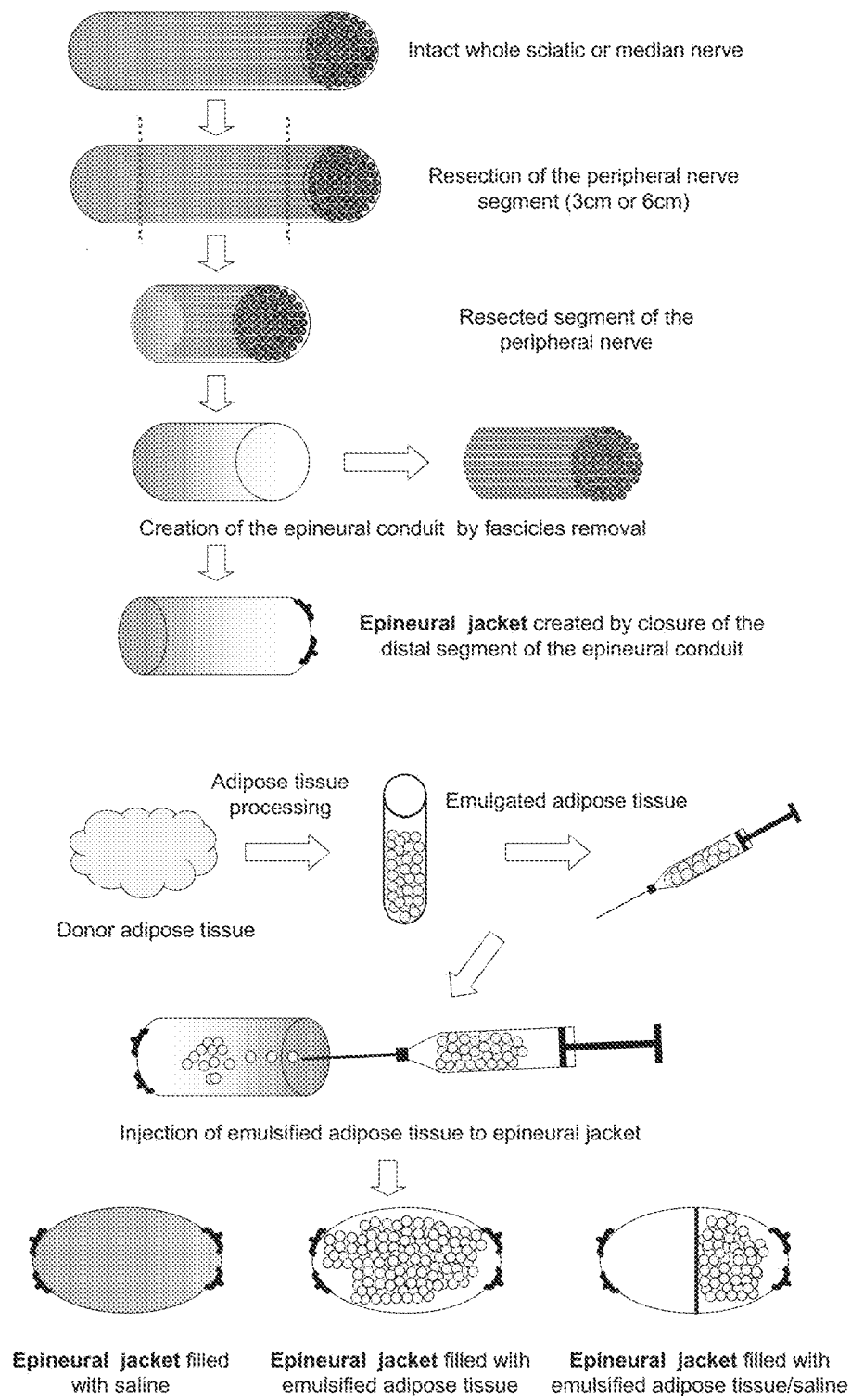
FIG. 1 is a schematic illustration of the generation of an epineural conduit that is used for maintenance of fat volume (an epineural fat jacket or epineural sausage).

Described herein is the use of an epineural sheath for fat delivery and/or fat volume maintenance and/or augmentation (e.g., fat transplantation; fat grafting) at one or more anatomical areas and spaces e.g., of tissue loss (e.g., occurring due to aging, burns and/or trauma) in an individual. As shown herein, the unique characteristics (e.g., angiogenic scaffold) and forms (e.g., conduit (tube; jacket); patch) of the epineural sheath allow for the introduction (e.g., delivery via implantation and/or injection) of fat to an individual in need thereof. The epineural sheath protects the fat at the site of delivery and creates a favorable environment for fat volume maintenance, and thus, can be used for cosmetic, reconstructive and/or regenerative medical applications (e.g., plastic surgery).

Specifically, an epineural sheath was tested for maintenance of adipose tissue volume in a rat sciatic nerve crush model. The crush injury was made with forceps to the epineurium of the sciatic nerve of rats and this crushed epineurium (epineural sheath) was then either left without coverage, wrapped with fat, wrapped with an isogenic epineural patch, or wrapped with an allogenic epineural patch to test their efficacy on nerve crush recovery. The finding of fat growth and expansion after application to the crushed nerve epineurium was unexpected. Further testing using an epineural jacket model comprising adipose tissue was done, which showed the utility of an epineural sheath comprising adipose tissue for delivery of fat, as well as maintenance and augmentation of fat in an individual in need thereof. As also shown herein, the fat volume increased over time at the one or more sites of the individual after the one or more epineural sheaths is introduced.

Accordingly, in one aspect, the invention is directed to a method of delivering fat to one or more sites in an individual in need thereof comprising introducing an effective amount of one or more epineural sheaths comprising adipose tissue to the one or more sites in the individual.

In another aspect, the invention is directed to a method of maintaining or augmenting (increasing; enhancing) fat volume at one or more sites in an individual in need thereof comprising introducing an effective amount of one or more epineural sheaths comprising adipose tissue to the one or more sites in the individual. The one or more epineural sheaths comprising adipose tissue is maintained under conditions in which the fat volume is maintained and/or augmented at the one or more sites in the individual.

Typically, nerve fibers are wrapped in a connective tissue called the endoneurium. Groups of fibers surrounded by their endoneurium are arranged in bundles called fascicles, and each fascicle is wrapped in connective tissue called the perineurium. The outermost covering around the entire nerve is the epineurium. As used herein an (one or more)

"epineural sheath" is an (one or more) epineurium of a (one or more) nerve. In a particular aspect, an isolated, naturally occurring epineurium sheath is used in the methods of the invention. A "naturally occurring" epineural sheath refers to an epineural sheath obtained from natural sources; that is, an epineural sheath that is not synthetic (non-synthetic). Epineural sheaths that are "isolated", include pure (essentially pure) epineural sheaths, that have been separated away from molecules and other tissues (e.g., endoneurium, perineurium, fasicles, blood components, inflammatory molecules) of their source of origin (e.g., an individual; an isolated nerve), and include epineural sheaths obtained by methods described herein or other suitable methods.

The epineural sheath can be obtained from a variety of nerves, such as nerves from invertebrates, vertebrates or a combination thereof. In one embodiment, the naturally occurring, isolated epineural sheath is obtained from (isolated from) a mammalian nerve such as a nerve of primate (e.g., human), porcine, canine, feline, bovine, and/or murine origin. In other embodiments, the epinueral sheath is an autologous epineural sheath, an allogenic epineural sheath, an isogenic epineural sheath, a xenogenic epineural sheath or a combination thereof. In a particular embodiment, the epineural sheath is obtained from a cadaver (e.g., a human cadaver). In addition, the epineural sheath can be obtained from a variety of type of nerves, such as from a sensory nerve and/or a motor nerve.

As described herein, all or a portion of an epineural sheath (e.g., a naturally occurring, isolated epineural sheath) can take a variety of shapes (regular, irregular) for use in the methods of the invention. The shape will depend upon a variety of factors, such as the purpose for which the adipose tissue is being introduced into the individual in need thereof (e.g., cosmetic surgery, reconstructive surgery, wasting disease) and/or the condition of the individual (e.g., patient). For example, one or more epineural sheaths can be used as a tube (e.g., a tube having one or two free ends or lumens; a hollow tube, also referred to as an epineural jacket), or one or more tubes can be longitudinally split and used as a flat rectangular sheath, also referred to herein as an epineural patch. In addition, one or more epineural sheaths can be formed into one or more strips, cords (e.g., twisted strips, plain or enriched with cells), patches, scaffolds (e.g., filled with adipose tissue, cells, growth factor), pastes, powders (e.g., in combination with a gel), putty(ies) or a combination thereof for use in the methods of the invention. As will be apparent to one of skill in the art, one or more of these forms can be achieved using one or more epineural sheaths (e.g., multiple epineural sheaths secured together, e.g., as a large sheet (e.g., patch) or secured together in multiple layers (e.g., layers of patches) and filled with powder, gel and/or factors that maintain and/or augment (increase, enhance) fat.

In the methods of the invention, all or a (one or more) portion of an (one or more) epineural sheath can be used in the methods. For example, in one aspect, one or more naturally occurring, isolated epineural tubes can be used in the methods. In another aspect, one or more naturally occurring, isolated epineural tubes can be split (e.g., longitudinally) and used as a (e.g., flat) rectangular sheath or patch in the methods. Various epineural sheaths, (e.g., tubes and patches) can be linked or custom designed (cut from whole sheath etc.). In one embodiment, two or more naturally occurring, isolated epineural tubes can be split e.g., longitudinally, thereby producing two or more rectangular sheaths, and the two or more rectangular sheaths (e.g., patches) can be used to make a large rectangular sheath (e.g., patch) or placed in layers (e.g., layers of patches; a "sandwich"). In another embodiment, the epineural tube can be split (e.g., longitudinally) into one or more strips.

As is apparent to one of skill in the art, different lengths and diameters of epineural sheaths may be used in the methods of the invention, and will depend upon a variety of factors, such as the reason for introducing the fat to the individual (e.g., cosmetic surgery, regenerative surgery) and/or the condition of the individual. In some aspects, the epineural sheath can be from about 1 mm to about 50 cm in length. In other aspects, the epineural sheath can be from about 1 cm to about 50 cm in width. In yet other aspect, the length and/or width of the epineural sheath can be about 1 mm, 2 mm, 3 mm, 4 mm, 5 mm, 6 mm, 7 mm, 8 mm, 9 mm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 22 cm, 24 cm, 26 cm, 28 cm, 30 cm, 32 cm, 34 cm, 36 cm, 38 cm, 40 cm, 42 cm, 44 cm, 46 cm, 48 cm, 50 cm).

In aspects in which the epineural sheath is an epineural tube, the tube diameters can be e.g., about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm).

In aspects in which the epineural sheath is a patch, the patch size can be about $1 \text{ mm}^2 \times 100 \text{ mm}^2$ or $1 \text{ cm}^2 \times 100 \text{ cm}^2$. For example, an epineural sheath in the form of an epineural patch can form a square patch of about 1×2 mm, 2×2 mm, 3×3 mm, 4×4 mm, 5×5 mm, 6×6 mm 7×7 mm, 8×8 mm, 9×9 mm, 10×10 mm, 20×20 mm, 30×30 mm, 40×40 mm, 50×50 mm, 60×60 mm, 70×70 mm, 80×80 mm, 90×90 mm, 100×100 mm, 2×2 cm, 2×2 cm, 3×3 cm, 4×4 cm, 5×5 cm, 6×6 cm 7×7 cm, 8×8 cm, 9×9 cm, 10×10 cm, 20×20 cm, 30×30 cm, 40×40 cm, 50×50 cm, 60×60 cm, 70×70 cm, 80×80 cm, 90×90 cm, 100 cm×100 cm, etc. Thus, the epineural sheath can take a variety of forms in various dimensions (e.g., a rectangle, circle, triangle, and the like) and will depend upon the application for which the spineural sheath comprising the adipose tissue is being used.

Methods for obtaining or harvesting isolated, naturally occurring epineural sheaths are provided herein, and are known to those of skill in the art. In addition, preservation methods to reduce immunogenicity for allografts and to keep stored epineural grafts for off shelf use and banking following methods are known. After harvesting, cyopreserved, cold stored, or lyophilized epineural sheaths can be used as different lengths, sizes, and widths. See for example U.S. Published Application No. 2011/0087338 and U.S. Published Application No. 2012/0171172, both of which are incorporated herein by reference.

Examples of methods for harvesting an isolated, naturally occurring epineural sheath from the a nerve (e.g., a sciatic nerve) are provided herein. As will be apparent to one of skill in the art, other methods can be used to harvest an isolated, naturally occurring epineural sheath from other sources using routine skills. In one embodiment, access to a peripheral nerve (e.g., sciatic nerve) is made by skin incision and subcutaneous tissue dissection down to the anatomical location of the nerve. At this level the nerve is cleared of all surrounding tissues by blunt dissection as far proximally as the sacral plexus and as far distally as its division into the terminal nerve branches. All collateral branches arising from the nerve throughout its length can be detached and used separately to create an epineurial sheath tubular grafts of different size diameters and lengths.

At this point the nerve is ready to be dissected out. The nerve is transected as proximal as is feasible at its origin from the sacral plexus, and then transected distally where the nerve divides into its terminal components, at the level of insertion into the muscle.

Depending upon the area of nerve harvest, the nerve can then be suspended on either a straight driver/irrigator with round tip (e.g., 30 gauge×25 mm depending on nerve diameter—the driver diameter is typically smaller than nerve diameter), on a curved/hook finished driver/irrigator, or on a screwdriver type of irrigator. The irrigator can be filled with chilled solution (either cryopreservation solution for long term storage, or nerve culture medium or combination of both—depending on the fate of graft) and kept moist on the dissection board by soaking it with 0.9% sodium chloride.

Under microscope or loop magnification the axons can then gently be teased from its epineural sheath with the use of circular motion of driver/irrigator and jeweler fine forceps pulling the sheath away from the axons and driver in the "devaginating maneuver", so that the axon fibers are pulled from the distal end whilst the epineural sheath is held from the proximal end on the driver/irrigator. Once all axons, the perineurium and the endoneurium are removed the intact, clear epineural sheath can be irrigated and left as a product of this process and is then inspected for integrity.

Following harvesting of the epineural sheath, the epineural sheaths can be stored for later use. For example, following harvesting, the epineural sheaths can be saturated with dimethlyosulfoxide (cryopreserving agent) and frozen (e.g., by computer controlled freezer (−196 degrees Celcius)) and stored in liquid nitrogen.

In the methods described herein, an effective amount of a composition comprising an (one or more) epineural sheath comprising adipose tissue is introduced (administered) to an individual in need thereof. As used herein "adipose tissue", also referred to as body fat or simply fat, is loose connective tissue composed mostly of adipocytes. In addition to mature adipocytes, adipose tissue can contain stem cells (e.g., adipose stem cells), preadipocytes, fibroblasts, vascular endothelial cells, vascular smooth muscle cells, and variety of immune cells (i.e. adipose tissue macrophages (ATMs)). Adipose tissue is derived from preadipocytes. Its main role is to store energy in the form of lipids, although it also cushions and insulates the body. Types of adipose tissue include white adipose tissue (WAT) and brown adipose tissue (BAT).

In some aspects, the epineural sheath for use in the methods described herein comprises (consists essentially of, consists of) adipose tissue, and in particular aspects, isolated adipose tissue. In other aspect, the epineural sheath for use in the methods described herein comprises (consists essentially of, consists of) adipocytes, and in particular aspects, isolated adipocytes in the methods described herein. As used herein "isolated", "purified", "substantially pure or purified" or "substantially isolated" adipose tissue or adipocytes refers to adipose tissue or adipocytes separated from the complex cellular milieu in which it naturally occurs, or chemical precursors or other chemicals when chemically synthesized or processed. Adipose tissue or adipocytes for use in the methods descried herein can comprise at least about 50%, 55%, 60%, 65%, 70%, 75%, 80%, 85%, 90%, 95%, 98% or 99% of all macromolecular species present.

A variety of methods can be used to obtain adipose tissue and/or adipocytes and are known to those of skill in the art. As is apparent to those of skill in the art, adipose tissue is easily accessible e.g., from one or more subcutaneous depots in one or more individuals, and can be harvested using a variety of techniques. Areas of one or more individuals from which adipose can be harvested include the abdomen, the thigh, the hip, the breast, a fat tumor (e.g., a lipoma) and/or the arm. Well known techniques such as surgical resection, liposuction (e.g., harvested during an adominoplasty), and/or cell-assisted lipotransfer methods which use, e.g., needles, cannulas, suction pressure, pumps and/or ultrasound can be used to obtain adipose tissue (e.g., Brown, S A, et al., *Plast. Reconstr. Surg.*, 126:1936 (2010); Gir, P, et al., *Plast Reconstr. Surg.*, 130:249 (2012) which are incorporated herein by reference). Thus, autologous fat is typically easily obtained.

In some aspects, the adipose tissue that is obtained can be used directly (not processed after harvesting), minimally processed, or more fully processed. In some aspects, the harvested fat is not processed and used directly as whole fat. In other aspects, the harvested fat is minimally processed by chopping into pieces. In yet other aspects, the harvested fat is more fully processed such as minced and/or emulgated (e.g., with saline to maintain volume). The harvested fat can also washed, centrifuged and treated to remove debris such as blood, infiltration fluid and/or cells.

As will be appreciated by those of skill in the art, the adipose tissue and/or adipocytes for use in the methods of the invention can be autologous, allogenic, isogenic, xenogenic or a combination thereof.

The volume of adipose tissue that can be present with and/or within the one or more epineural sheaths will vary and will depend upon the intended used. In one aspect, the volume of adipose tissue is from about 0.5 cc to about 500 cc. In other aspects, the volume of adipose tissue is about 1 cc, 10 cc, 20 cc, 40 cc, 60 cc, 80 cc, 100 cc, 120 cc, 140 cc, 160 cc, 180 cc, 200 cc, 220 cc, 240 cc, 260 cc, 280 cc, 300 cc, 320 cc, 340 cc, 360 cc, 380 cc, 400 cc, 420 cc, 440 cc, 460 cc, 480 cc or 500 cc.

Depending upon the use for which the epineural sheath comprising adipose tissue is being used and/or the needs of in the individual, the fat volume in each of the one or more epineural sheaths that is introduced into an individual can be maintained for a period of days, weeks, months or years. In some aspects, the fat volume can be maintained in the individual for a period of about 1 month to about 5 years or longer. In other aspects, the fat volume can be maintained in the individual for a period of about 6 months to about 4 years. In other aspects, the fat volume can be maintained in the individual for a period of about 1 year to about 3 years. In still other aspects, the fat volume can be maintained in the individual for a period of about 1.5 years to about 2 years.

The epineural sheath comprising adipose tissue is maintained under conditions in which fat is delivered, maintained and/or augmented in the individual in need thereof. For example, as will be apparent to one of skill in the art, in some embodiments, after introducing the epineural sheath comprising adipose tissue in an individual as described herein, the area of the fat graft (e.g., the surgical area) can be maintained under conditions to (in an environment that) promote healing, and prevent or minimize scar formation and/or infection, of the area.

The methods described herein can further comprise contacting the epineural sheath (e.g., filling the graft; coating the sheath) with other agents that aid in the delivery, maintenance and/or augmentation of fat. Examples of such agents include cells (e.g., stem cells, progenitor cells, mesenchymal stem cells, adipose stem cells, preadipocytes, fibroblasts, vascular endothelial cells, bone marrow stem cells, immune cells), growth factors, angiogenic factors, pro-angiogenic factors, cytokines or a combination thereof. "Angiogenic factors" or "pro-angiogenic factors" are substances (e.g., polypeptide, lipid) that causes the growth of new blood vessels. Examples of angiogenic factors include vascular endothelial growth factor (VEGF), von Willebrandt Factor (vWF), CD31, acidic and basic fibroblast growth factor, angiogenin, and transforming growth factors alpha and beta.

The epineural sheath comprising adipose tissue can be introduced into (administered to) the individual in need thereof using a variety of methods. For example, the epineural sheath comprising adipose tissue can be locally introduced (e.g., implanted (e.g., laparoscopy) and/or injected at the site of a surgical incision) into the individual in need thereof. In some aspects, the epineural sheath comprising adipose tissue is introduced to the site of the individual using sutures. In a particular aspect, the epineural sheath comprising adipose tissue can be introduced using a microsurgical technique with microsurgical sutures (4-6 sutures 10/0), a gluing technique (e.g., using different types of tissue sealants or glues), a staple technique, or a combination thereof. In particular aspects, the epineural sheath can overlie the site of introduction e.g., in a dimension from about 1 mm to 20 mm, about 3 mm to about 15 mm, about 5 mm to about 10 mm, and about 7 mm to about 12 mm, 1 cm to 20 cm, about 3 cm to about 15 cm, about 5 cm to about 10 cm, and about 7 cm to about 12 cm, etc.

For example, using standard surgical technique, an epineural sheath of sufficient size (e.g., ranging from 1×1 cm up to 10×10 cm), and thickness (single layer; multiple layer patch) which effectively covers the site of the individual into which the adipose tissue is introduced can be secured (e.g., using suture) into the desired position. The effectiveness of the seal can be augmented with various commercially available glues, such as fibrin glue, staplers, and other adhesive materials. Alternatively, the epineural patch can be placed topically as an "on lay graft" at the site of the individual into which the adipose tissue is introduced relying on mechanical, chemical or electrostatic adhesive forces to prevent dislodgment, or can be placed topically at the site of the individual into which the adipose tissue is introduced and secured with commercially available glue, such as fibrin glue. The epineural sheath (e.g., epineural patch) can be fashioned in such a manner where part or all of the down side is covered with an adhesive substance, such as fibrin glue. It can then placed topically at the site of the individual into which the adipose tissue is introduced and secured to the underlying tissues by the adhesive properties of the glue.

As described herein, the epineural sheaths are introduced to the one or more sites of the individual, and the adipose tissue can be introduced into the one or more the epineural sheaths before, at the time, or after, the epineural sheaths are introduced to the one or more sites of the individual. Adipose tissue can be within or around (coated on) the epineural sheath. For example, in one aspect, when the epineural sheath is a tube (jacket), the adipose tissue can be introduced (inserted e.g., injected) within, and/or coated on the interior and/or exterior of the epineural tube. After the adipose tissue is introduced within and/or on the epineural tube, one or both ends of the epineural tube can be sealed.

In another aspect, when the epineural sheath is a patch, the adipose tissue can be inserted (e.g., injected) above, below (under), around and/or between one or more epineural patch layers ("sandwich"). As with the epineural tube, the epineural pathc can also be coated with adipose tissue.

As described herein, the epineural sheath (e.g., an epineural patch) can be used in a single layer or in multiple layers, and can be placed topically at the site of the individual into which the adipose tissue is introduced relying on mechanical, chemical or electroadhesive forces to prevent dislodgment. The epineural sheath can be placed topically on the one or more sites and secured with commercially available sutures, staplers and glue, such as fibrin glue. The epineural sheath can be fashioned in such a manner where part or all of the down side is covered with an adhesive substance, such as fibrin glue. It is then placed topically at the site of the individual into which the adipose tissue is introduced and secured to the underlying neural tissues by the adhesive properties of the glue or by sutures.

The epineural sheath can be used to introduce fat to an individual in need thereof at any of a variety of sites (anatomical sites) in the body where, for example, fat volume delivery, maintenance or augmentation is needed and/or desired. For example, the epineural sheath comprising adipose tissue can be used for both cosmetic and reconstructive indications. Uses for fat grafting include repair of contour and/or volume deformities and/or defects, facial augmentation (e.g., postirradiation/postsurgical reconstruction of the head/neck), facial lipodystrophy, lip augmentation, correction of defects, rejuvenation of extremities (hand/leg rejuvenation), lower limb atrophy, breast reconstruction (e.g., postirradiation/postsurgical reconstruction of the breast) and/or augmentation, gluteal augmentation, penile enlargement, and/or aesthetic improvement. Thus, the epineural sheath can be used to introduce fat to the face (e.g., eyes, lips, cheeks, chin), chest (e.g., breast, pectorals), back, extremities (e.g., legs, arms) and the like.

The epineural sheath comprising adipose tissue can be introduced into the one or more sites of the individual via injection, surgical implantation (e.g., laparoscopic surgery) or a combination thereof. In one aspect, the epineural sheath can be dispersed and or layered at the site in the individual.

The methods of the invention can also comprise contacting the epineural sheath comprising adipose tissue with, or administering to the individual, one or more immunosuppressants, particularly in embodiments in which the epineural sheath is of non-autologous origin. Examples of immunosuppressants or immunosuppressant protocols which can be used include different types of antibodies (e.g., Thymoglobulin, Camptah, Daclizumab, etc.) and alpha/beta TCR/CsA protocol, Cyclosporine A protocol, Tacrolimus, Sirolimus, Rapamycin, Celcept, mycofolenate moefetil, and/or steroids. In the methods described herein, it will be apparent to one of skill in the art that the factors and/or immunosuppressants can be used prior to, at the time of, or after introduction of the epineural sheath comprising adipose tissue into the individual. See, for example, Scharpf, J., et al., *Microsurgery*, 26:599-607 (2006).

As is apparent to those of skill in the art, the epineural sheath and/or adipose tissue can also comprise a label for detection/visualization either ex vivo or in vivo. For example, cells can be labeled with PKH-26, which stays visible for over 100 days.

As one of skill will also appreciate, a variety of volume-enhancing agents or fillers used in fat transplantation (fat grafting) can be used in combination with the epineural sheath comprising adipose tissue. An example of such volume-enhancing agents or fillers is hyaluronic acid.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined via the use of well known risk factors. The effective amount of a (one or more) particular compound is determined, in the final analysis, by the physician in charge of the case, but depends on factors such as the exact condition to be treated, the severity of the condition from which the patient suffers, the chosen route of administration, other drugs and treatments which the patient may concomitantly require, and other factors in the physician's judgment.

As used herein, an "effective amount" or "therapeutically effective amount" means an amount of the active compound that will elicit the desired biological or medical response in a tissue, system, subject, or human, which includes alleviation of the symptoms, in whole or in part, of the condition being treated.

The epineural sheath comprising adipose tissue can be administered in a single dose (e.g., in a day) or in multiple doses. In addition, the epineural sheath comprising adipose tissue can be administered in one or more days (e.g. over several consecutive days or non-consecutive days, weeks, months, years).

EXEMPLIFICATION

Example 1

As proof of principal, use of the epineural sheath for maintenance of adipose tissue volume was tested in a rat sciatic nerve model previously described in see U.S. Published Application No. 2011/0087338 which is incorporated herein by reference in its entirety. The crush injury is made with forceps to the epineurium of the sciatic nerve and this crushed epineurium (epineural sheath) is then either left without coverage (see Group 1 below), wrapped with fat (see Group 2 below), wrapped with an isogenic epineural patch (see Group 3 below) or wrapped with an allogenic epineural patch (see Group 4 below) to test their efficacy on nerve crush recovery. The finding of fat growth and expansion after application to the crushed nerve epineurium was unexpected and thus was further tested using an epineural jacket model for its applicability for fat volume, maintenance and augmentation.

The segment of rat sciatic nerve was harvested, suspended on a straight irrigator and, using a pull-out technique (see U.S. Published Application No. 2011/0087338 which is incorporated herein by reference in its entirety), the fascicles of the rat sciatic nerve were removed, thereby creating an empty epineural sheath tube or jacket (see FIG. 1). The epineural sheath tube was then opened creating an epineural patch (see FIG. 2) which was tested in a rat sciatic nerve crush model (e.g., see Gudemez, E., et al., *Microsurgery*, 22:234-241 (2002)).

Four experimental groups (6 rats in each group) were tested (see FIG. 3).

The Group 1 rats served as a control of epineural sheath crush. The sciatic nerve, and thus the epineural sheath of the sciatic nerve, was crushed. The crush site was left untreated.

For the Group 2 rats, fat (a fat patch) obtained from the gluteal region of each rat (autologous fat) was wrapped around the crushed sciatic nerve.

For the Group 3 rats an isogenic epineural sheath (ES), harvested from the sciatic nerve of Lewis rats of the same strain (genetically identical) as described in US Published Application No. 2011/0087338, was wrapped around the crushed sciatic nerve.

For the Group 4 rats an allogenic epineural sheath, harvested from the sciatic nerve of MHC mismatched ACI rats as described in US Published Application No. 2011/0087338, was wrapped around the crushed sciatic nerve.

In the rat sciatic nerve proof or principal experiment fat was used as control material to protect the crushed nerve from the scar environment after being crushed and compared with the protective properties of the epineural sheath.

The results of the study confirmed not only the maintenance of fat volume applied to the epineural sheath but also a several-fold increase of fat volume over the 6-12 weeks period shown both macroscopically and confirmed by fat graft weight (FIG. 4).

VEGF Fluorescent Staining of Frozen Samples:

Collected fresh tissues were snap frozen in liquid nitrogen, embedded in OCT compound in cryomolds. Each sample was cut in 5 µm thick sections and mounted on superfrost plus slides. Before staining each slide was warmed at room temperature for 30 minutes and fixed in ice cold acetone for 10 minutes. After this step each sample was washed 3 times in PBS for 5 minutes. Sections were incubated in serum blocking solution (5% donkey serum in PBS and 0.1% Triton X-100) for 30 minutes at room temperature. After blocking of non-specific binding of immunoglobulin all sections were incubated with VEGF primary antibody (Santa Cruze, cat. #: sc-6313, 1:50 dilution) for 1 hour at room temperature. Sections were than rinsed 3 times in PBS for 5 minutes at room temperature. Secondary antibody was applied for 30 min at room temperature (Santa Cruze, cat. #: sc-2024, donkey anti goat IgG-FITC, dilution 1:200). After that step samples were rinsed 3 times in PBS solution for 5 minutes at room temperature. At the final step slides were counterstain with DAPI solution (Vectashield, H-1200) and observed under fuorescent microscope.

Figure 5:
FIG. 5 show vascular endothelial growth factor (VEGF) immunostaining results.

The immunostaining showed heightened expression of the VEGF within the adipose tissue (FIG. 5) which correlated macroscopically with neovascularization of the fat patch shown in FIG. 4. More expression of VEGF in isogenic ES rats (Group 3) as well as control rats (Group 1) confirmed that the epineural sheath, either crushed as in the control group (Group 1) or as an iogenic sheath wrapped around the crushed nerve, is constitutively expressing VEGF which supports nerve regeneration. In contrast, the fat used in the Group 2 rats did not express VEGF, and thus, does not support nerve regeneration. The experiment showed that there is low amounts of VEGF in fat.

Example 2 Use of the Epineural Jacket (Epineural Tube) to Deliver and Maintain Fat Volume (See FIG. 1)

Preparation and Implantation of the Epineural Sausage and Fat Tissue

Figure 6:
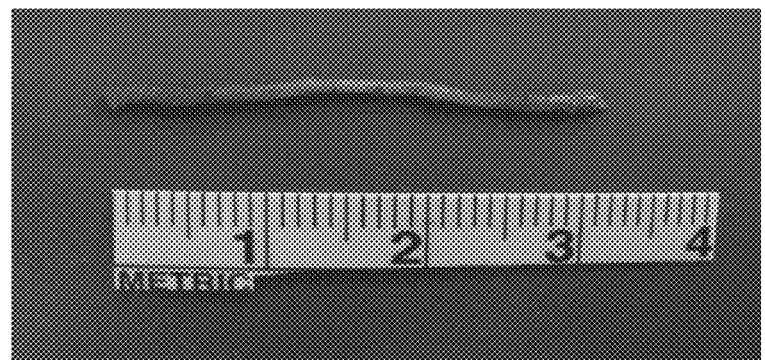
FIG. 6 shows a 3 cm long sciatic nerve segment.

A 3 cm long segment of sciatic nerve (before branching to common peroneal nerve and tibial nerve) from a rat was harvested with minimally traumatic technique as described in Example 1. FIG. 6 shows the sciatic nerve segment.

Figure 7A:
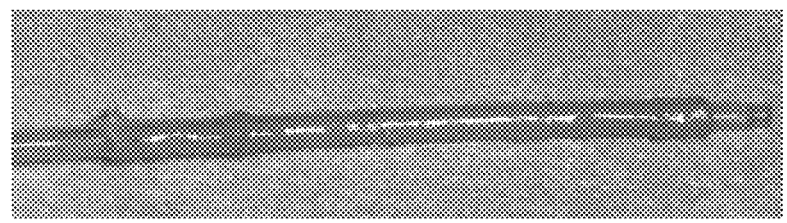
FIGS. 7A-7B show an empty epineural tube.
Figure 7B:
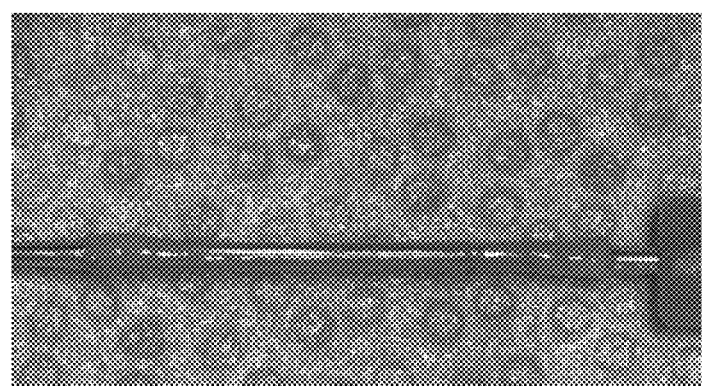

The sciatic nerve was suspended on a straight irrigator (30 ga) and while suspended the nerve fascicles were removed with the aid of fine surgical forceps from both the proximal and distal ends. This resulted in an empty epineural tube. Any visible branches were dissected and closed to mitigate leakage. FIGS. 7A and 7B show the empty epineural tube.

Figure 8:
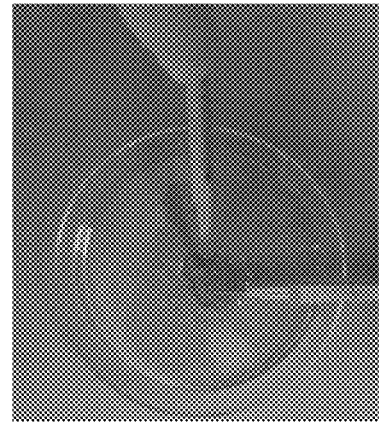
FIG. 8 shows fat tissue chopping.
Figure 9:
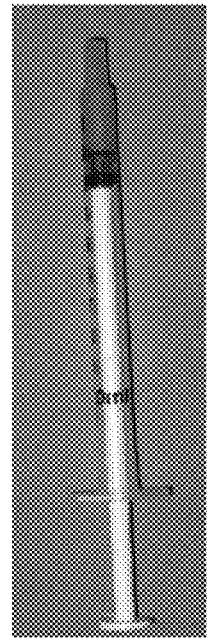
FIG. 9 shows chopped fat inside a syringe.
Figure 10:
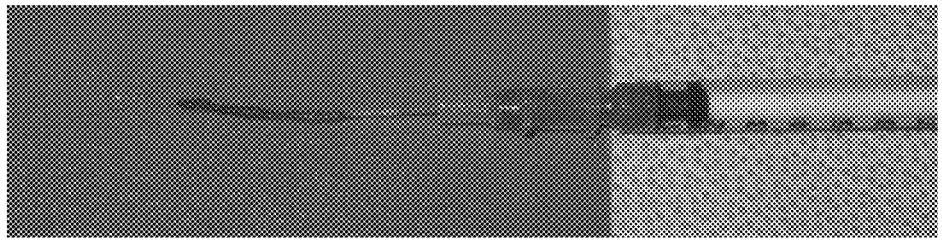
FIG. 10 shows fat tissue implantation inside an epineural tube.

Fat tissue was harvested from the gluteal region of rats, divided into small pieces using a scalpel. FIG. 8 shows division (e.g., mincing; chopping) of the fat tissue into small pieces. The chopped/minced fat was transferred to a syringe. FIG. 9 shows "chopped" fat tissue inside the syringe. After tying one end of the epineural tube, the epineural tube was filled with fat tissue. FIG. 10 shows fat tissue implanted inside the epineural tube.

Figure 11A:
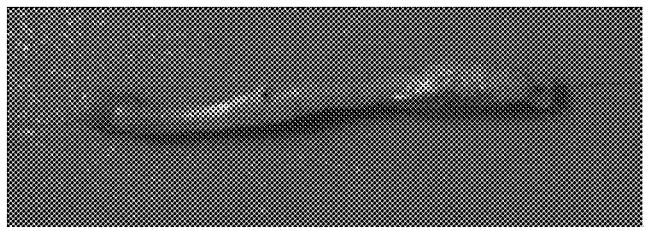
FIGS. 11A-11C show an empty epineural jacket.
Figure 11B:
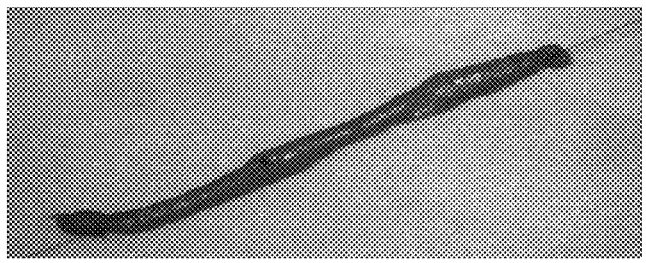
Figure 11C:

The other end of the epineural tube was closed and the epineural jacket (epineural sheath tube+fat tissue) was created. FIGS. 11A-11C show the epineural fat jacket.

Figure 12A:
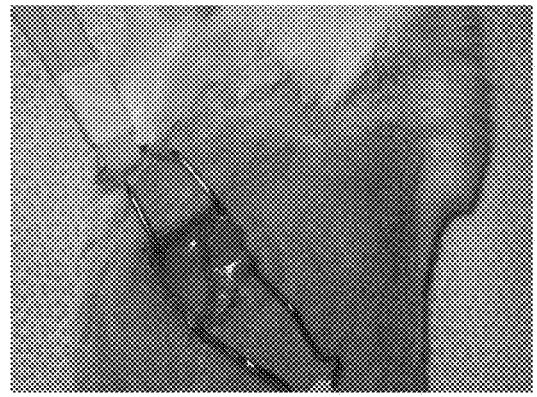
FIGS. 12A-12B show the epineural jacket implanted into the dorsal subcutaneous region of a rat.
Figure 12B:
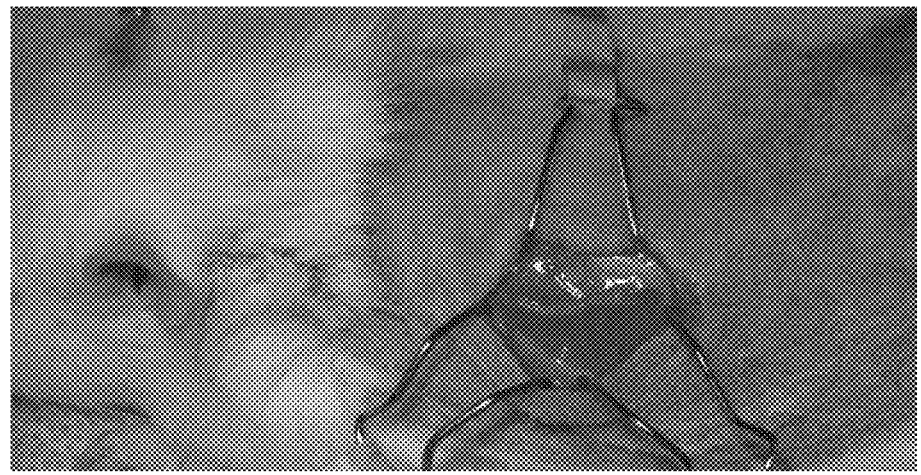

The epineural jacket was implanted into the dorsal subcutaneous region of a rat via 2 cm skin incision. FIGS. 12A and 12B show the epineural jacket filled with fat implanted into the dorsal subcutaneous region of the rat.

Figure 2:
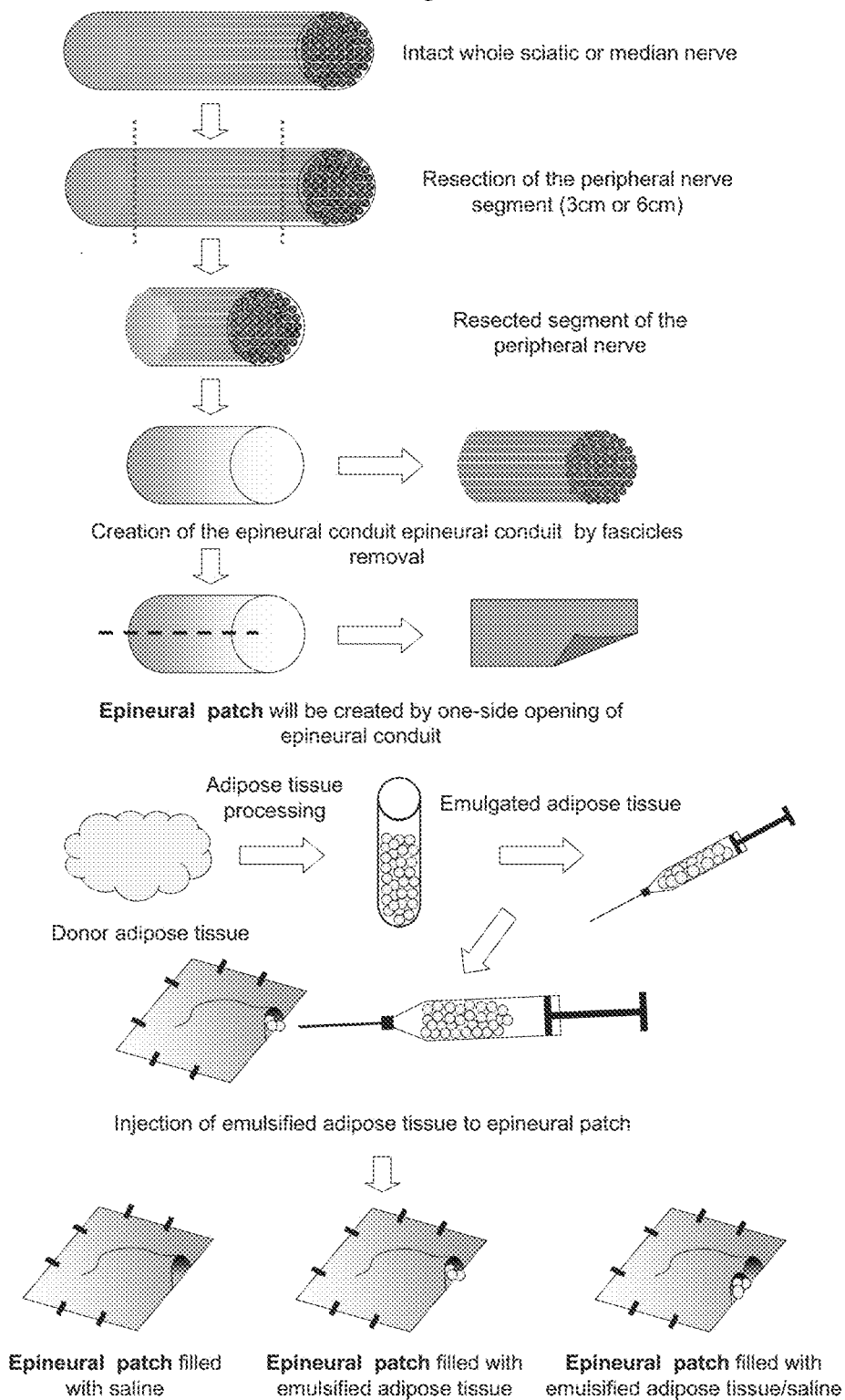
FIG. 2 is a schematic illustration of the generation of an epineural patch that is used for maintenance of fat volume.
Figure 13:
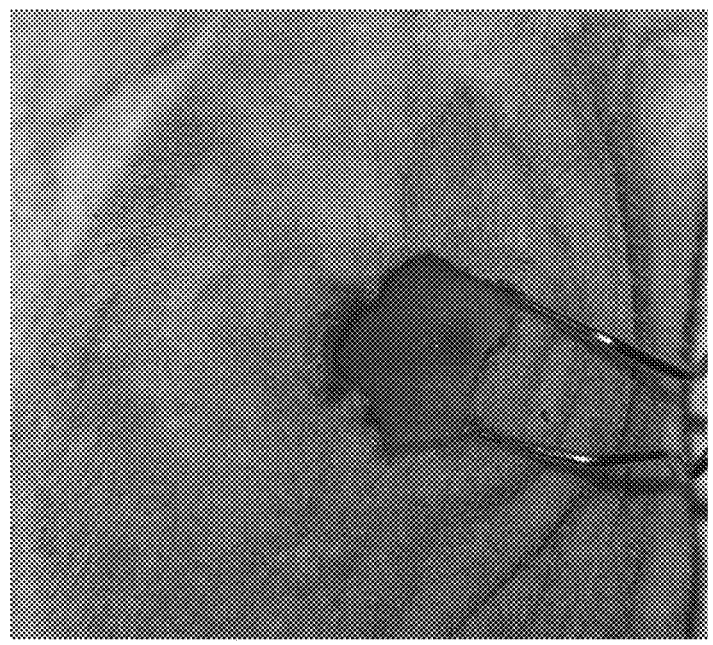
FIG. 13 shows fat tissue implanted into the dorsal subcutaneous region of a rat via a 2 cm incision.

Fat tissue alone without epineural sheath coverage was implanted into the dorsal subcutaneous region of the rat via 2 cm incision to serve as a control for the epineural fat jacket group and for assessment of the fat volume maintenance using the epineural sheath jacket (FIG. 1) or patch (FIG. 2). See FIG. 13 for the control group of fat alone implantation. After one week, the epinueral jacket filled with fat as well as fat alone were resected and weighed on a scale.

Animal #851 represents the surgical in vivo representation of FIG. 1, where an epineural tube filled with fat tissue is implanted in vivo.

| Rat #851 groups | Day 0 before implantation | 1 week after implantation |
|---|---|---|
| Group 1 Epineural jacket with fat (epineural tube + fat tissue) | 0.020 g (0.013 g fat tissue) | 0.021 g |
| Group 2 Control - Fat tissue only without epineural coverage | Sample 1 - 0.013 g<br>Sample 2 - 0.013 g | 0.010 g<br>0.010 g |
| Group 3 - Control -Minced Epineural Tube mixed with fat tissue without epineural coverage | 0.020 g (0.013 fat tissue) | 0.010 g |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of delivering fat to one or more sites in an individual in need thereof comprising introducing an effective amount of one or more epineural sheaths comprising adipose tissue to the one or more sites in the individual via injection, insertion, surgical implantation, surgical placement, surgical attachment or a combination thereof, wherein, with respect to the individual (a) the one or more epineural sheaths are autologous, allogenic, isogenic, or a combination thereof and (b) the adipose tissue is autologous, allogenic, isogenic, or a combination thereof, and further wherein the fat volume increases over time at the one or more sites of the individual after the one or more epineural sheaths is introduced.

2. The method of claim 1 wherein the adipose tissue is autologous adipose tissue, allogenic adipose tissue, isogenic adipose tissue, or a combination thereof.

3. The method of claim 1 wherein the volume of adipose tissue in each of the one or more epineural sheaths is about 0.5 cc to about 300 cc.

4. The method of claim 1 wherein the fat volume in each of the one or more epineural sheaths is maintained in the individual for about 1 month to about 5 years.

5. The method of claim 1 wherein the one or more epineural sheaths further comprise one or more stem cells, growth factors that are angiogenic or pro-angiogenic factors, cytokines or a combination thereof.

6. The method of claim 5 wherein the stem cells are mesenchymal stem cells, adipose stem cells or a combination thereof.

7. The method of claim 1 wherein one or more of the epineural sheaths are about 1 cm to about 50 cm in length.

8. The method of claim 1 wherein one or more of the epineural sheaths are in the form of an epineural tube, an epineural patch, an epinueral paste, an epineural powder or a combination thereof.

9. The method of claim 8 wherein the adipose tissue is inserted within one or more of the epineural tubes and after insertion of the adipose tissue, one or both ends of the one or more epineural tubes are sealed.

10. The method of claim 9 wherein one or more of the epineural patches are introduced to the one or more sites of the individual and the adipose tissue is inserted under one or more of the epineural patches at the time, or after, the epineural patches are introduced to the one or more sites of the individual.

11. The method of claim 8 wherein the epineural patch is from about 1 mm to about 10 cm in length and about 1 mm to about 10 cm in width.

12. The method of claim 1 wherein one or more of the epineural sheaths are an autologous epineural sheath an allogenic epineural sheath, or a combination thereof.

13. The method of claim 1 wherein one or more of the epineural sheaths are obtained from a cadaver.

14. The method of claim 1 wherein one or more of the epineural sheaths are obtained from a peripheral nerve or a median nerve.

15. The method of claim 1 wherein one or more of the sites in the individual comprises the individual's head, face, neck, chest, back, one or more extremities or a combination thereof.

16. The method of claim 1 wherein the individual is a human.

17. The method of claim 1 wherein the one or more epineural sheaths further comprises one or more volume enhancing agents.

* * * * *